United States Patent
Heuser et al.

(10) Patent No.: US 9,259,340 B2
(45) Date of Patent: Feb. 16, 2016

(54) METHODS AND SYSTEMS FOR BYPASSING OCCLUSIONS IN A FEMORAL ARTERY

(71) Applicants: Richard R. Heuser, Phoenix, AZ (US); James D. Joye, Saratoga, CA (US); Kumar Ganesan Jambunathan, Sunnyvale, CA (US); Eugene E. Reis, San Jose, CA (US); Richard A. Lotti, Santa Cruz, CA (US)

(72) Inventors: Richard R. Heuser, Phoenix, AZ (US); James D. Joye, Saratoga, CA (US); Kumar Ganesan Jambunathan, Sunnyvale, CA (US); Eugene E. Reis, San Jose, CA (US); Richard A. Lotti, Santa Cruz, CA (US)

(73) Assignee: PQ BYPASS, INC., Sunnyvale, CA (US)

( * ) Notice: Subject to any disclaimer, the term of this patent is extended or adjusted under 35 U.S.C. 154(b) by 438 days.

(21) Appl. No.: 13/868,804

(22) Filed: Apr. 23, 2013

(65) Prior Publication Data

US 2014/0142677 A1 May 22, 2014

Related U.S. Application Data

(60) Provisional application No. 61/637,129, filed on Apr. 23, 2012.

(51) Int. Cl.
*A61F 2/95* (2013.01)
*A61B 17/12* (2006.01)
(Continued)

(52) U.S. Cl.
CPC .............. *A61F 2/95* (2013.01); *A61B 17/12045* (2013.01); *A61B 17/12136* (2013.01); *A61M 25/0194* (2013.01); *A61B 2017/00252* (2013.01); *A61B 2017/00986* (2013.01); *A61B 2017/1107* (2013.01); *A61B 2017/1139* (2013.01); *A61B 2017/22044* (2013.01); *A61B 2017/22095* (2013.01); *A61B 2019/5466* (2013.01); *A61M 25/0032* (2013.01); *A61M 25/0108* (2013.01); *A61M 25/04* (2013.01);
(Continued)

(58) Field of Classification Search
CPC ................... A61B 17/12045; A61B 17/12136; A61B 2017/00252; A61B 2017/00986; A61B 2017/1107; A61B 2017/1139; A61B 2017/22044; A61B 2017/22095; A61B 2019/5466; A61F 2/95; A61M 25/0032; A61M 25/0108; A61M 25/1011; A61M 25/0194; A61M 2025/0096; A61M 2025/0197
See application file for complete search history.

(56) References Cited

U.S. PATENT DOCUMENTS

| | | |
|---|---|---|
| 5,078,735 A | 1/1992 | Mobin-uddin |
| 5,211,683 A | 5/1993 | Maginot |

(Continued)

FOREIGN PATENT DOCUMENTS

WO    WO 2007/127802 A2    11/2007

OTHER PUBLICATIONS

International search report and written opinion dated Aug. 21, 2013 for PCT/US2013/037858.

*Primary Examiner* — Ryan Severson
*Assistant Examiner* — Christian Knauss
(74) *Attorney, Agent, or Firm* — Wilson Sonsini Goodrich & Rosati

(57) ABSTRACT

A system for deploying a stent-graft from the femoral artery into the femoral vein and back into the femoral artery in order to bypass a femoral occlusion comprises a penetration catheter and a guidewire capture and stabilization catheter. The penetration catheter may be advanced contralaterally to a location above the occlusion and the capture and stabilization catheter may be introduced upwardly through the femoral vein. The penetration tool on the penetration catheter is used in multiple steps to deploy guidewires which are then used to deploy the stent-graft in the desired location.

19 Claims, 13 Drawing Sheets

(51) Int. Cl.
  *A61M 25/04* (2006.01)
  *A61M 25/00* (2006.01)
  *A61M 25/01* (2006.01)
  *A61M 25/10* (2013.01)
  *A61B 17/00* (2006.01)
  *A61B 17/11* (2006.01)
  *A61B 19/00* (2006.01)
  *A61B 17/22* (2006.01)

(52) U.S. Cl.
  CPC ... *A61M 25/1011* (2013.01); *A61M 2025/0096* (2013.01); *A61M 2025/0197* (2013.01)

(56) References Cited

U.S. PATENT DOCUMENTS

| | | |
|---|---|---|
| 5,830,222 A | 11/1998 | Makower |
| 6,042,598 A | 3/2000 | Tsugita et al. |
| 6,068,638 A | 5/2000 | Makower |
| 6,190,353 B1 | 2/2001 | Makower et al. |
| 6,231,587 B1 | 5/2001 | Makower |
| 6,379,319 B1 | 4/2002 | Garibotto et al. |
| 6,464,665 B1 | 10/2002 | Heuser |
| 6,475,226 B1 | 11/2002 | Belef et al. |
| 6,508,824 B1 | 1/2003 | Flaherty et al. |
| 6,544,230 B1 | 4/2003 | Flaherty et al. |
| 6,579,311 B1 | 6/2003 | Makower |
| 6,585,650 B1 | 7/2003 | Solem |
| 6,655,386 B1 | 12/2003 | Makower et al. |
| 6,694,983 B2 | 2/2004 | Wolf et al. |
| 6,719,725 B2 | 4/2004 | Milo et al. |
| 6,976,990 B2 | 12/2005 | Mowry |
| 7,004,173 B2 | 2/2006 | Sparks et al. |
| 7,083,631 B2 | 8/2006 | Houser et al. |
| 7,134,438 B2 | 11/2006 | Makower et al. |
| 7,316,655 B2 | 1/2008 | Garibotto et al. |
| 7,374,567 B2 | 5/2008 | Heuser |
| 7,729,738 B2 | 6/2010 | Flaherty et al. |
| 8,075,584 B2 | 12/2011 | Barbut |
| 2002/0123698 A1* | 9/2002 | Garibotto ............... A61B 17/11 600/585 |
| 2004/0158143 A1* | 8/2004 | Flaherty ............... A61B 1/3137 600/407 |
| 2008/0154172 A1 | 6/2008 | Mauch |
| 2009/0264826 A1 | 10/2009 | Thompson |
| 2010/0036475 A1 | 2/2010 | Castaneda |
| 2012/0239137 A1 | 9/2012 | Heuser et al. |

* cited by examiner

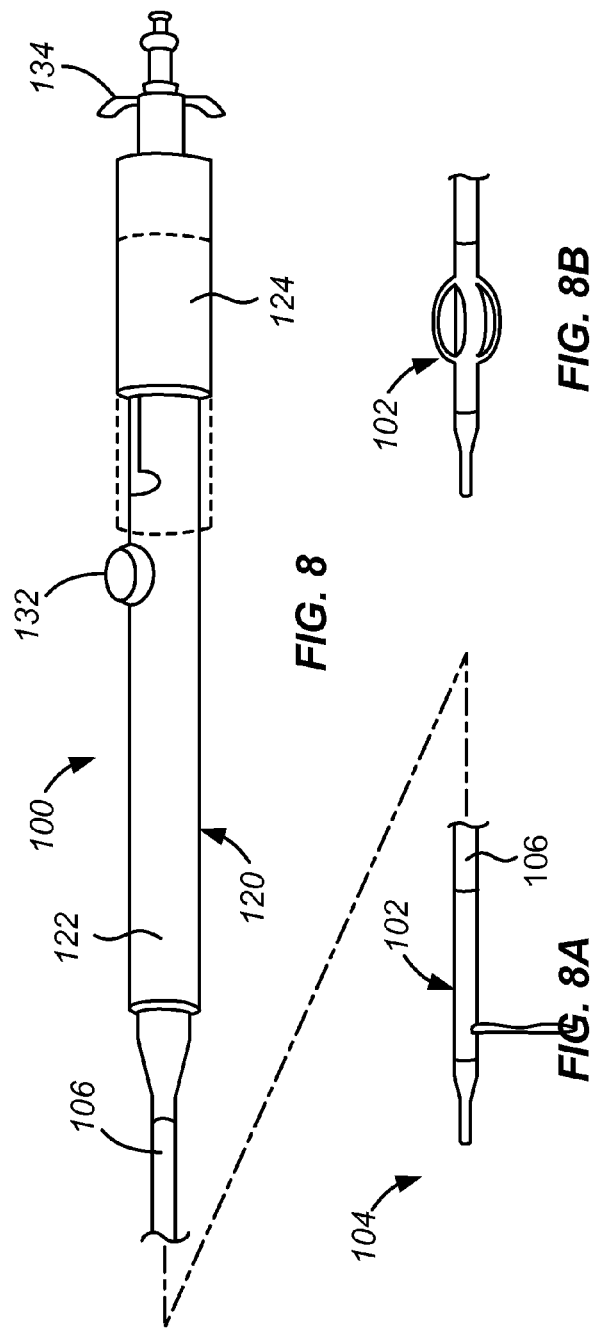

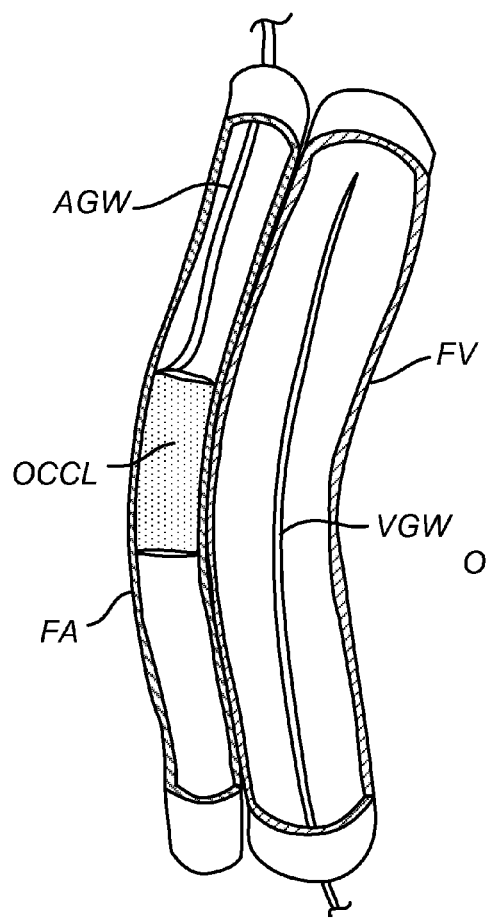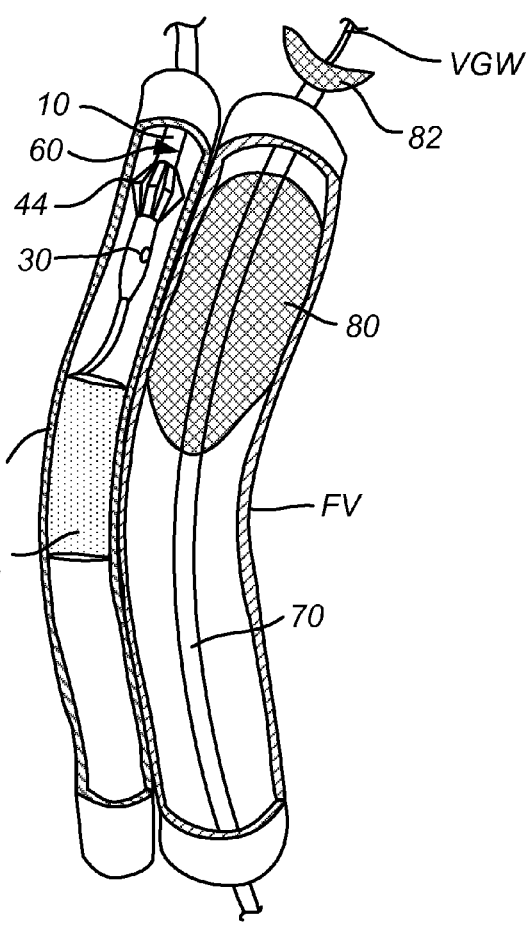
FIG. 12A  FIG. 12B

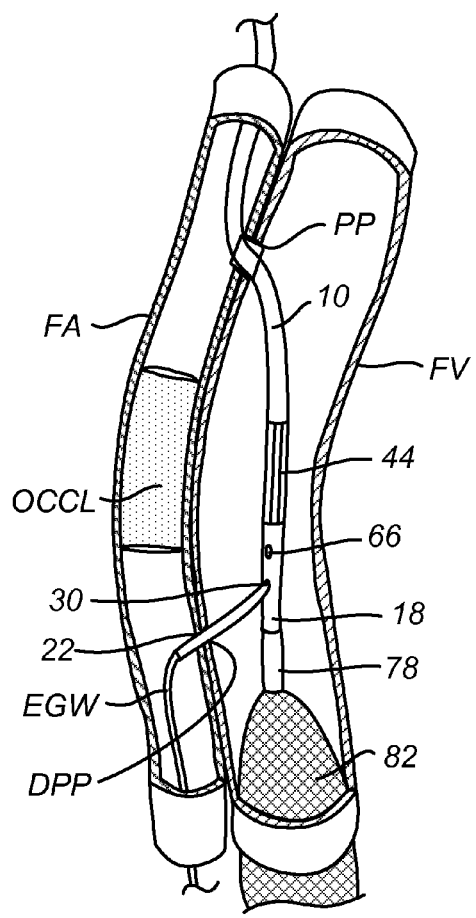 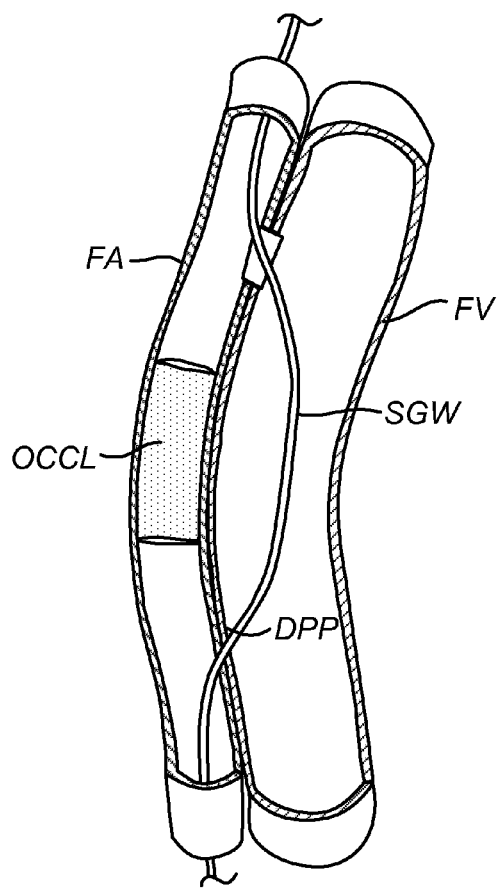
*FIG. 12G*      *FIG. 12H*

METHODS AND SYSTEMS FOR BYPASSING OCCLUSIONS IN A FEMORAL ARTERY

CROSS-REFERENCE TO RELATED APPLICATIONS

This application claims priority to U.S. Provisional Application No. 61/637,129, filed Apr. 23, 2012, the entire content of which is incorporated herein by reference.

BACKGROUND OF THE INVENTION

1. Field of the Invention

The present invention relates generally to medical methods and devices. More particularly, the present invention relates to methods and devices for the endovascular placement of a stent-graft from an artery, through an adjacent vein, and back to the artery in order to bypass an occlusion in the artery, typically a femoral artery.

Peripheral arterial occlusive disease results from atherosclerotic processes which cause a blockage or stenosis within a peripheral artery, typically a femoral artery, most commonly the superficial femoral artery. As the disease progresses, resistance to blood flow down the patient's leg reduces distal perfusion of the leg. In the most severe cases, the disease can lead to limb ischemia which can have serious complications, including gangrene and loss of the leg.

Peripheral arterial occlusive disease in the femoral artery can be treated in many of the same ways as arterial disease elsewhere in the body. Endarterectomy and atherectomy can both be used to remove the occlusive deposits and restore blood flow. Bypass grafts may also be placed from a location proximal to the occlusion to a location distal to the occlusion in order to provide an unobstructed path for blood to flow in the artery. Such bypass grafts are most commonly placed in open vascular surgeries where the bypass grafts may be attached to the femoral or other artery by conventional anastomic connections. More recently, it has been proposed to perform such procedures endovascularly to place a bypass stent-graft from the artery, through an adjacent vein, and back to the artery in order to bypass the occlusion.

Of particular interest to the present invention, Dr. James Joye has performed such endovascular stent-graft bypass procedures using commercially available catheters and tools.

While such protocols are very effective in the hands of a highly skilled vascular surgeon, they are lengthy, can be difficult to perform, and many surgeons would not feel confident trying to perform these procedures using conventionally available catheters and tools. For these reasons, it would be desirable to provide improved protocols and specialized catheters and surgical tools which reduce the technical difficulty of performing such endovascular stent-graft femoral bypass procedures. At least some of these objectives will be met by the inventions described herein below.

2. Description of the Background Art

Systems and methods for placing stent-grafts for bypassing peripheral and other occlusions are described in U.S. Pat. Nos. 5,078,735 and 5,211,683. A particular method for performing an external femoropopliteal bypass graft is described in WO2007/127802 and US 2010/0036475. U.S. Pat. Nos. 6,464,665 and 7,374,567, both describe catheters useful for capturing a needle and placing a stent across adjacent vessels. Other relevant patents include U.S. Pat. Nos. 5,830,222; 6,068,638; 6,190,353; 6,231,587; 6,379,319; 6,475,226; 6,508,824; 6,544,230; 6,655,386; 6,579,311; 6,585,650; 6,694,983; 6,719,725; 6,976,990; 7,004,173; 7,083,631; 7,134,438; 7,316,655; and 7,729,738.

SUMMARY OF THE INVENTION

The present invention provides methods and systems for bypassing occlusions in a peripheral artery. The peripheral artery will most commonly be a femoral artery, such as a superficial femoral artery or a common femoral artery, but could also be an iliac artery, a popliteal artery, a posterior tibial artery, a peroneal artery, an anterior tibial artery, and the like. For consistency, references below will typically be made to the femoral artery. The methods comprise a series of steps which are performed endovascularly in a femoral artery, typically the superficial femoral artery including the popliteal artery which is an extension of the superficial femoral artery, as well as in one or more adjacent femoral veins including a popliteal vein which is an extension of the femoral vein. The methods comprise forming a proximal penetration from the femoral artery to an adjacent femoral vein at a location above the occlusion. A penetration guidewire is advanced down the femoral artery, through the proximal penetration, and into the femoral vein. Typically, the penetration guidewire will be advanced contralaterally over the iliac arch from the opposite leg of the patient.

After the penetration guidewire has been advanced into the femoral vein, the penetration guidewire will be pulled through an external penetration below the occlusion, typically in the popliteal vein. The penetration catheter is then advanced over the penetration guidewire from the femoral artery into the femoral vein, and a penetration tool carried by the penetration catheter is penetrated from the femoral vein into the femoral artery at a location below the occlusion to form a distal penetration. After both the proximal and distal penetrations are formed, a graft placement guidewire is positioned from the femoral artery through the proximal penetration, down the femoral vein, and through the distal penetration back into the femoral artery. A stent-graft is then deployed from a catheter introduced over the stent-graft placement guidewire to complete the bypass of the occlusion.

As used herein and in the claims, the directions of "up," "upward," "down," and "downward" are intended to mean the directions relative to the patient's head and feet, where the head will generally be considered up or upward and the feet will be considered down or downward.

In a specific aspect of the method of the present invention, the proximal penetration is formed by advancing a penetration catheter down the femoral artery to a location above the occlusion and penetrating a penetration tool carried by the penetration catheter from the femoral artery into the femoral vein. Typically, the penetration catheter will be advanced over a guidewire which has been previously placed from a contralateral access point, over the iliac arch, and into the femoral artery above the occlusion. In preferred aspects, the penetration catheter used for forming the proximal occlusion is the same penetration catheter as is used for forming the distal penetration.

Once the penetration tool has been penetrated from the femoral artery into the femoral vein, the penetration guidewire may be advanced through the penetration tool and into the femoral vein. As set forth above, a distal end of the penetration guidewire is then pulled from the femoral vein through an external penetration below the occlusion.

In a preferred aspect of the method, the penetration catheter will be stabilized as the penetration tool is advanced from the femoral artery into the femoral vein. Stabilizing typically comprises expanding a stabilizing element on the catheter to engage the inner wall of the femoral artery and hold a shaft of the penetration catheter immobile as the penetration tool is advanced. This stabilizing element can be any expansible component, typically being a balloon, braid, or preferably a malecot (a molly bolt-like mechanical structure which expands radially as it is axially contracted).

Pulling the penetration guidewire through the external penetration typically comprises advancing a venous catheter through the external penetration and up the femoral vein (typically starting in a popliteal or tibial vein) to position a guidewire capture tool on the venous catheter above the occlusion. It is to be understood, of course, that the occlusion is in the femoral artery, so the venous catheter will be advanced to a position within the femoral vein which is across or adjacent to the occlusion in the femoral artery.

Once in position, a capture tool on the venous catheter will be used to capture the penetration guidewire. The venous catheter is then withdrawn from the femoral vein to pull the penetration guidewire though the external penetration. The capture tool may comprise any component or element capable of securing the penetration guidewire, typically being an expandable braid where capturing comprises collapsing the braid over the penetration guidewire after the guidewire has been advanced into the braid, typically using the penetration element on the penetration catheter. A sheath may be advanced over the exterior of the capture tool to help secure the guidewire to the capture tool as the venous catheter is withdrawn In preferred embodiments, the penetration catheter is stabilized as the penetration tool is advanced from the femoral vein back into the femoral artery. Such stabilization is typically accomplished by advancing the venous catheter through the external penetration and up the femoral vein to connect or otherwise couple to the distal end of the penetration catheter. By coupling to the penetration catheter, the venous catheter, which will typically have its expansible braid expanded, will hold and center the distal end of the penetration catheter as the penetration tool is advanced. Placing the stent-graft placement guidewire typically comprises advancing the stent-graft placement guidewire (or an exchange wire) through a hollow lumen in the penetration tool after said tool has been advanced from the femoral vein into the femoral artery. Typically, an 0.014 in. or other small exchange wire is first deployed through penetration tool, and is then exchanged for an 0.035 in. or other larger stent-graft placement guidewire which is used to position a stent-graft delivery catheter to deliver the stent graft(s) as described more fully below. Use of the heavier guidewire is advantageous since the stent-graft placement guidewire will not be controlled at its distal end.

Deploying the stent-graft over the stent-graft placement guidewire will typically comprise releasing the stent-graft from constraint so that the stent-graft then can self-expand. For example, the stent-graft may be composed of a nitinol or other shape-memory material, typically covered by a graft material, and be constrained in a tubular sheath of a stent-graft placement catheter which is advanced over the stent placement guidewire. The sheath may then be retracted to deploy the stent. Alternatively, in some instances, the stent graft may be balloon expandable or expandable for axial contraction, e.g., using a tether or other puller to draw the end of the scaffold together to cause radial expansion. In some cases, one stent will be sufficient to form the bypass graft. For longer occlusions, two or more stent grafts may be deployed in an overlapping fashion. In still other embodiments, it may be desirable to initially place covered or uncovered stents, either self-expanding or balloon expandable, in either or both of the anastomic penetrations between the artery and vein before deploying the stent-graft.

The present invention further comprises systems for placing a stent-graft between a femoral or other peripheral artery and a femoral or other peripheral vein. Systems comprise a penetration catheter and a guidewire and stabilization catheter (which can act as the venous catheter in the methods described above). The penetration catheter carries a penetration tool adapted to penetrate and adjacent arterial and venous wall and to advance a guidewire between the femoral artery and the femoral vein. The guidewire capture and stabilization catheter is adapted to (1) capture a guidewire advanced by the penetration catheter from the femoral artery to the femoral vein and (2) align the penetration catheter within the femoral vein while the penetration tool penetrates and advances a guidewire into the femoral artery.

The penetration catheter will typically comprise a shaft having a proximal end, a distal end, a guidewire lumen, and a penetration tool lumen. Penetration tool will be reciprocatably disposed in the penetration tool lumen, and the distal end of the penetration tool deflects laterally as the tool is advanced distally. The penetration tool will typically have a guidewire lumen which is in addition to the guidewire lumen formed in the shaft of the penetration catheter itself. The guidewire lumen in the penetration tool allows placement of a guidewire through a penetration formed by the tool while the catheter shaft is placed over a separate guidewire. Optionally, the penetration catheter may further comprise a stabilizing element near the distal end of the shaft, typically being a balloon, an expandable braid, a malecot, or the like. Preferably, the stabilizing element comprises a malecot where the penetrating element advances through components or leaves of the malecot when the malecot is deployed. In other embodiments, the stabilizing element may comprise a pair of axially spaced-apart malecots.

The guidewire and stabilization catheter will typically comprise a shaft having a proximal end, a distal end, and a guidewire lumen. A guidewire capture structure will be disposed near the distal end of the shaft. Preferably, the guidewire capture structure comprises a radially expandable braid, where the guidewire can be captured by contracting the braid after the guidewire has entered the braid. Optionally, the guidewire capture structure may comprise a pair of axially spaced-apart radially expandable braids. The use of two braids allows the guidewire capturing stabilization catheter to orient itself within the venous lumen when it is capturing the guidewire and also when it couples to the penetration catheter to stabilize the penetration catheter. In such cases, the distal end of the guidewire capturing stabilization catheter will be adapted to removably couple to the distal end of the penetration catheter to provide the desired stabilization. The guidewire and stabilization catheter may optionally include a reciprocatable exterior sheath which can be advanced over the braid or other capture structure both to help collapse the capture structure (to lower the profile for withdrawal from the vein) and to fix the guidewire to the capture structure as the catheter is being withdrawn.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 8 and 8A-8E illustrate a sixth embodiment of a penetration catheter of the present invention similar to that previously described with reference to FIGS. 6A-6B.

FIGS. 12A-12J illustrate an exemplary method of the present invention using the penetration catheter and the guidewire capture and stabilization catheter for implanting a bypass graft from the femoral artery into the femoral vein and back from the femoral vein into the femoral artery to bypass the occlusion in the femoral artery.

DETAILED DESCRIPTION OF THE INVENTION

Figure 1:
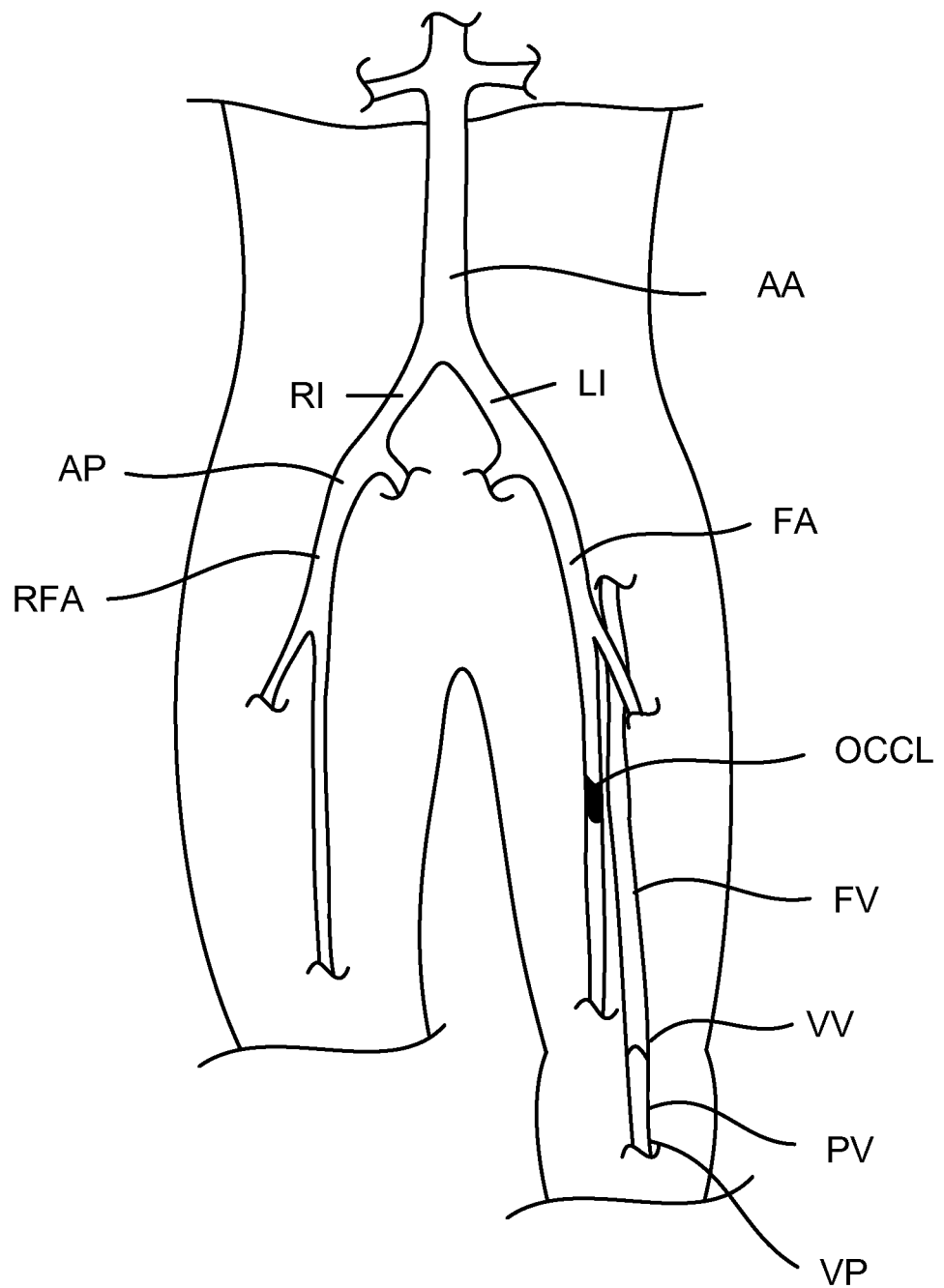
FIG. 1 illustrates the target anatomy to be treated by the methods and apparatus of the present invention including a femoral artery having an occlusion and an adjacent femoral vein which is used to bypass the occlusion. The view is anterior-posterior and would be reversed if taken from a supine point-of-view.

Referring to FIG. 1, the methods and systems of the present invention are particularly suitable for bypassing an occlusion OCCL present in a femoral artery FA. As shown in FIG. 1, the occlusion OCCL is present in the right femoral artery, but the methods and systems would be suitable for treating occlusions in the left femoral artery, as well as all of the other peripheral arteries listed above. The anatomy includes a right femoral artery RFA, a left femoral artery FA which both branch from the abdominal aorta AA through the right iliac artery RI and the left iliac artery LI. As will be described in more detail below, the methods of the present invention will typically be performed by introducing catheters from the "contralateral" artery into the "ipsilateral" artery over the branch between the iliacs.

The femoral artery FA runs parallel to the femoral vein FV. This is true, of course, in both legs although only the left femoral vein FV is shown in FIG. 1. The femoral vein FV extends downwardly and becomes the popliteal vein PV below the knee. Unlike the arteries, the femoral vein includes venous valves VV which inhibit retrograde flow of the venous blood away from the heart. As will be described in more detail below, the present invention relies on advancing catheters though the popliteal vein PV and the femoral vein FV (and sometimes the tibial or other veins) only in an upward direction which minimizes any damage to the venous valves VV.

Figure 2:
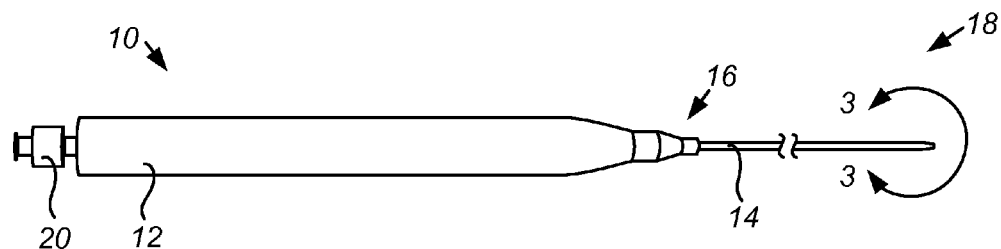
FIG. 2 illustrates the general features of a penetration catheter, which is part of the system of the present invention.

Referring now to FIG. 2, a penetration catheter 10 constructed in accordance with the principles of the present invention comprises a handle 12, a shaft 14 having a proximal end 16 and a distal end 18, where a handle is attached to the proximal end of the shaft. A penetration guidewire port 20 is located at a proximal end of the handle and allows for a penetration guidewire to be advanced through a penetration tool 22 (FIG. 3C) as described in more detail below.

The penetration catheter 10 and handle 12 will include a number of mechanisms of a type which are conventionally employed in catheter construction and do not need to be described in detail herein. For example, the catheter shaft 14 will be adapted to be introduced over a placement guidewire, typically an 0.014 in. guidewire. The catheter shaft 14 may be adapted for a conventional over-the-wire placement, but will more usually utilize a guidewire port which is positioned near to the distal tip of the catheter, typically being located from 10 cm-50 cm from the distal tip. Such shortened guidewire lumens are usually referred to as "rapid exchange" guidewire lumens. In specific embodiments, the penetration catheter will be adapted to be introduced contraltareally over the iliac function, usually have a length of 150 cm. The penetration tool will typically be a curved, resilient needle which deploys over a radially outward curved path as it is advanced. The handle will also include mechanisms for advancing and retracting the penetration tool 22 as well as for expanding and contracting stabilization elements, such as expandable braid members 24 and 26, as illustrated in FIGS. 3A-3C.

Figure 3A:
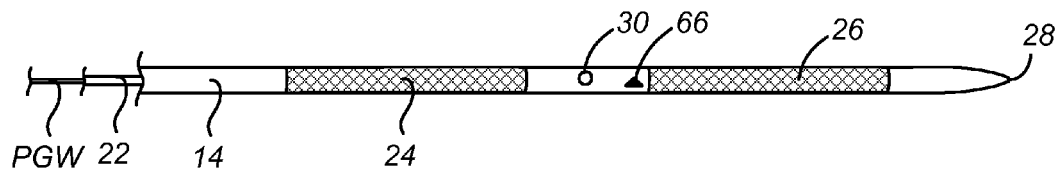
FIGS. 3A-3C illustrate a first embodiment of a distal end of the penetration catheter of FIG. 2 including a pair of expandable braid stabilization elements and a laterally extendable penetration tool.
Figure 3B:
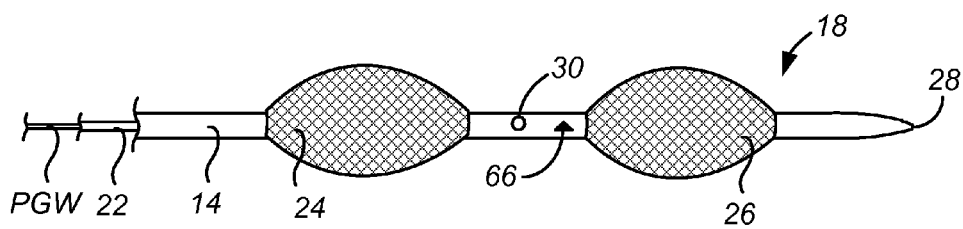
Figure 3C:
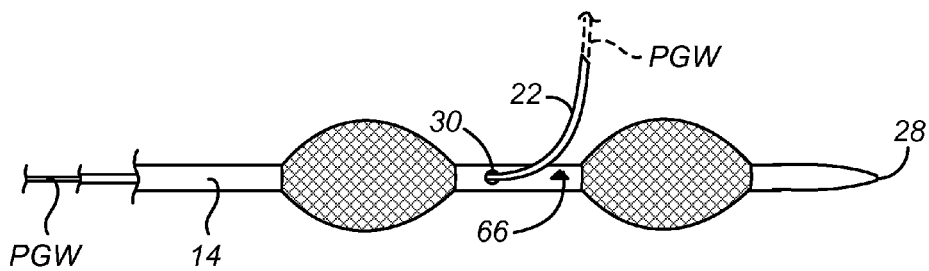

Referring now to FIGS. 3A-3C, a first embodiment of the distal end 18 comprises a pair of axially spaced-apart expandable braid members 24 and 26 located proximal to and distal to a penetration tool port 30, respectively. The expandable braid members 24 and 26 are configured in a radially contracted or collapsed configuration, as shown in FIG. 3A, for initial introduction into the patient's vasculature over a conventional guidewire, as described in more detail below. The catheter shaft 14 will have a guidewire lumen which terminates in distal tip guidewire port 28. The guidewire lumen will typically have a rapid exchange configuration with a second guidewire port somewhere on the shaft (not illustrated herein), typically located from 10 cm to 50 cm in a proximal direction from the distal tip guidewire port 28. The penetration tool 22 is slidably or reciprocatably mounted within an internal lumen (for example lumen 32 in FIG. 8). The penetration tool 22 is initially retracted within the penetration tool lumen, as shown in FIG. 3A, and may be distally advanced so that it emerges in a generally lateral direction, as illustrated in FIG. 3C. The stabilization braids are radially expandable to assume the configurations illustrated in FIGS. 3B and 3C in order to stabilize and immobilize the catheter within the femoral artery as the penetration tool 22 is being advanced, as will be described in greater detail below.

The distal end 18 of the penetration catheter 10 may assume a variety of different and alternative configurations. For example, in FIG. 4, a distal end 18a is illustrated where shaft 14a includes a single expandable stabilization element shown to be an inflatable balloon 36. The balloon is shown in a deflated configuration in full line and an inflated configuration in a broken line. The penetration tool port 30a is shown to be distal of the inflatable balloon 36, but in other embodiments it could be located proximally of the balloon.

Figure 4:
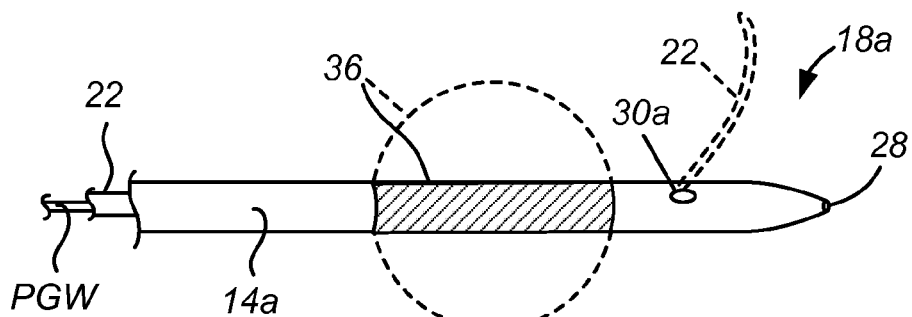
FIG. 4 illustrates a second embodiment of the distal end of the penetration catheter of FIG. 2.
Figure 5:
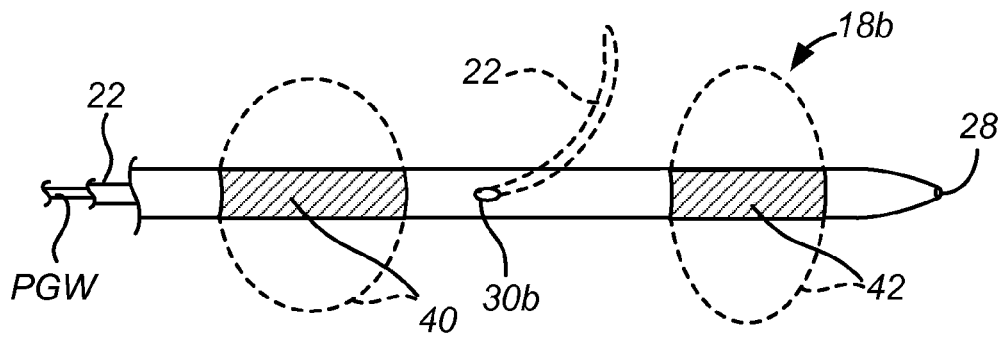
FIG. 5 illustrates a third embodiment of the distal end of the penetration catheter of FIG. 2.

A third embodiment of the catheter distal end is illustrated in FIG. 5. Catheter distal end 18b includes a proximal inflatable balloon 40 and a distal inflatable balloon 42, with the balloons shown in their deflated configurations in full line and their inflated configurations in broken line. The penetration tool port 30b is located between the balloons 40 and 42 so that penetration tool 22 is laterally advanced in the region between said balloons. The use of the proximal balloon 40 and distal balloon 42 provides enhanced stabilization relative to the use of a single balloon as illustrated in FIG. 4. The use of a single balloon, in contrast, is advantageous in that it is easier to position and manipulate.

Figure 6A:
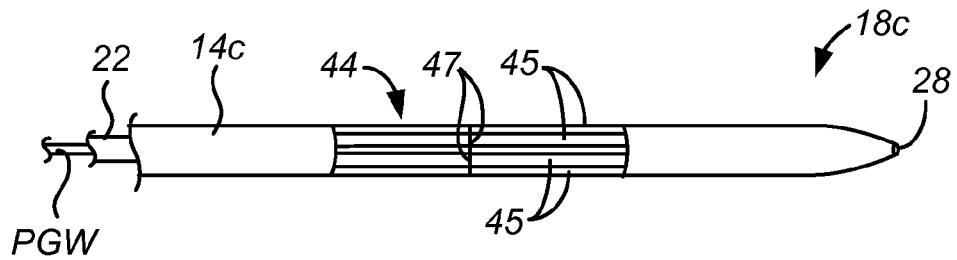
FIGS. 6A and 6B illustrate a fourth embodiment of the distal end of the penetration catheter of FIG. 2.
Figure 6B:
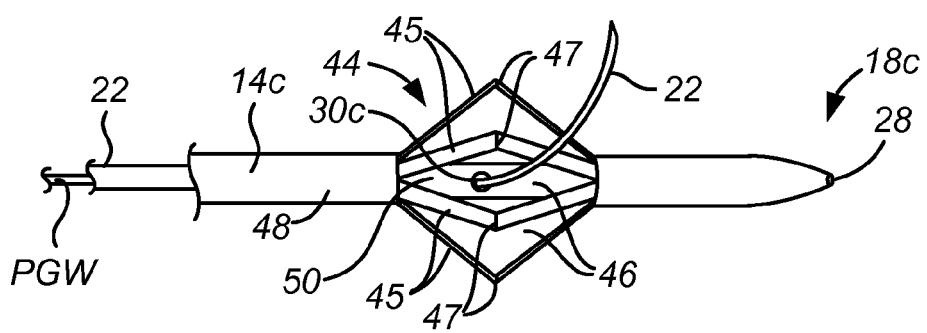

A fourth embodiment, of the distal end of catheter shaft 14 is illustrated in FIGS. 6A and 6B. The distal end 18c comprises an expandable cage structure 44 formed in the shaft 14c. Cage 44 is introduced in the radially collapsed configuration, as shown in FIG. 6A, and may be expanded to a radially expanded configuration, as shown in FIG. 6B, by shortening the shaft to shorten the individual elements 45 so that they fold about a center point 47 which is typically scored or otherwise weakened. To facilitate such foreshortening, the shaft 14c will typically include both an outer tubular member 48 and an inner tubular member 50 so that the outer member may be pulled back (in a proximal direction) relative to the inner member in order to foreshorten the cage structure 44. The construction of such expandable cages is well known in the in the medical arts. Such cages are generally referred to as malecots.

Once the cage structure 44 is expanded, the penetration tool 22 may be advanced through the penetration tool port 30c so that the tool extends through gaps 46 between the individual elements 45. As with all embodiments described thus far, the penetration tool will be emerging along an arcuate path which lies in a plane which is generally perpendicular to an axis of the shaft 14. The illustration in FIG. 6B, is somewhat distorted in order to show that the tool is emerging through the gaps. In a more correct perspective, the tool 22 would be shown to be emerging directly out of the paper toward the viewer, but such a depiction would be harder to understand.

Figure 7A:
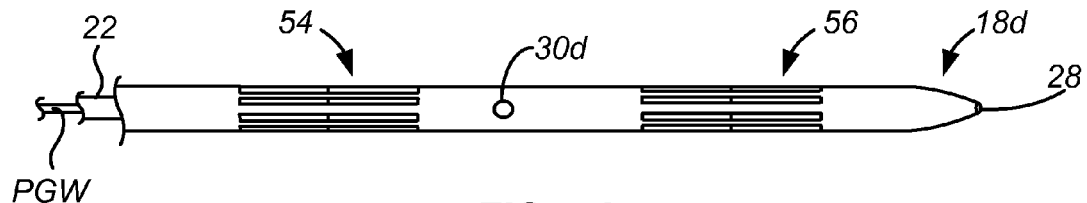
FIGS. 7A and 7B illustrate a fifth embodiment of the distal end of the penetration catheter of FIG. 2.
Figure 7B:
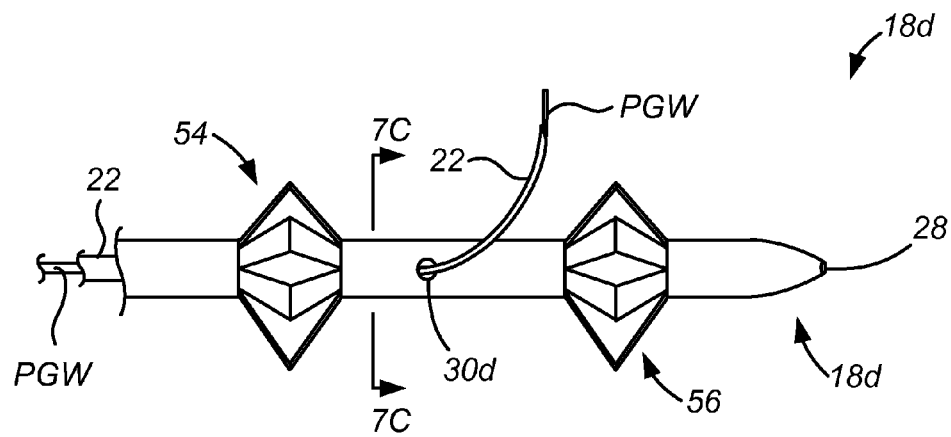

A fifth embodiment of the distal end of the penetration catheter shaft 14 is illustrated in FIGS. 7A and 7B. The distal end 18d includes both a proximal expandable cage 54 and a distal expandable cage 56 where the penetration tool port 30d is disposed between the two expandable cages. The expandable cages 54 and 56 are both constructed similarly to the cage 44 illustrated in FIGS. 6A and 6B, and will typically be expandable using a coaxial tubular arrangement as previously described. The use of two expandable cages is advantageous as it provides greater stabilization, while the use of a single expandable cage is advantageous in that it is easier to deploy and less constricted by limitations in the vasculature. As with certain of the previous illustrations, the radial direction of the advanced penetration tool 22 shown in FIG. 7B is somewhat misleading as the tool will usually emerge along an arc in a plane which is perpendicular to the axis of the catheter.

Figure 7C:
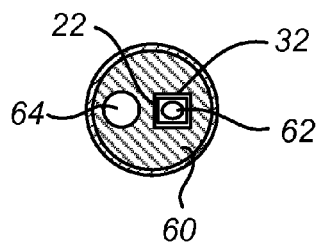
FIG. 7C is a cross-sectional view taken along line 7C-7C of FIG. 7B illustrating a non-circular penetration tool lumen which is utilized to maintain alignment of a non-circular penetration tool.

Referring now to FIG. 7C, the catheter shaft may include an insert or body element 60 which includes a penetration tool lumen 32 for advancing and retracting the penetration tool 22. In a specific embodiment, the penetration tool lumen 32 may have a non-circular cross-section, shown to be rectangular, which holds a penetration tool 22 having a similar cross-sectional shape in a constant orientation relative to the catheter shaft as the tool is advanced. Such a geometry helps assure that the penetration tool 22 emerges in a direction within a plane perpendicular to the axis of the catheter. Also shown in FIG. 7C, the penetration tool will include a lumen 62 which receives the penetration guidewire PGW (FIG. 7B), allowing the penetration guidewire PGW to be advanced from the penetration tool 22 after the penetration tool has been introduced to an adjacent vessel lumen. The penetration and catheter shaft will also include a main or positioning guidewire lumen 64 which terminates in the proximal guidewire port 28 which allows the penetration catheter to be initially introduced to and located within the vasculature. As described previously, the guidewire lumen 64 will typically be configured as a short length, rapid exchange lumen of a type well known in the art.

Figure 8D:
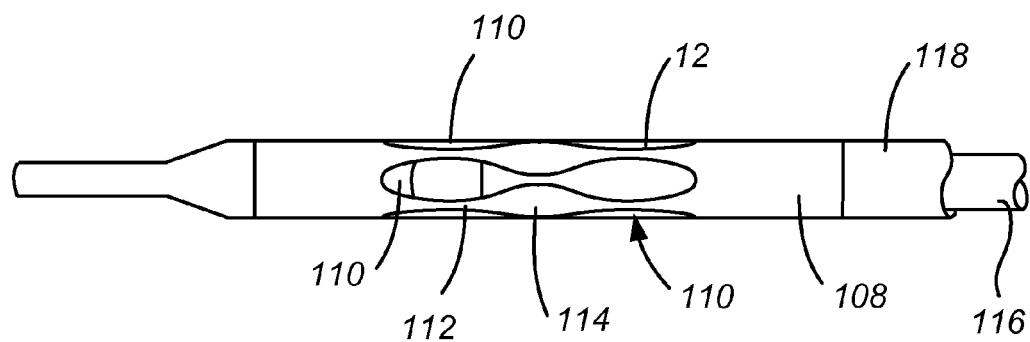
Figure 8E:
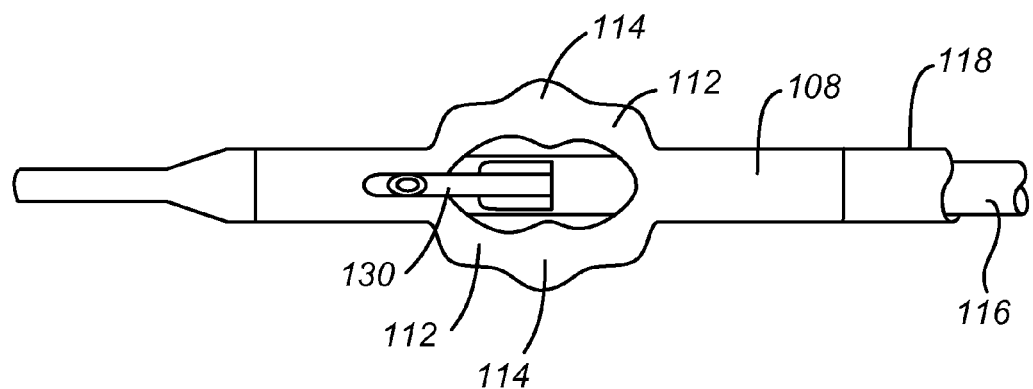

Referring now to FIGS. 8A-8F, another embodiment of a penetration catheter 100 having a single expandable cage or malecot 102 at a distal end 104 of its shaft 106 is illustrated. As best seen in FIGS. 8D and 8E, the cage 102 is formed from a thin walled polyimide sleeve 108. Four slots 110 are laser cut into the sleeve leaving four struts 112 having widened mid-sections 114. A distal end of the sleeve is attached to a distal end of an inner member 116 of the shaft 106 while a proximal end of the sleeve is attached to a distal end of an outer member 118 of the shaft. Thus, the struts 112 of the sleeve may be radially expanded by advancing the inner member relative to the outer member, as shown in FIG. 8E. The narrower regions of the struts on either side of the widened mid-sections provide preferential bending to promote uniform expansion. Use of the thin wall sleeve 108 is advantageous as it minimizes the width or "profile" of the penetration catheter, typically allowing delivery through an 8 F introducer sheath. In an exemplary embodiment, the cage will have a diameter when collapsed of about 7 F (2.4 mm) and will be expandable to a diameter of 8 mm.

The penetration catheter 100 includes a handle assembly 120 attached to a proximal end of the shaft 106. The handle includes a cylindrical body 122 having a slidable cage deployment and spring-loading ring 124 near its proximal end. When the ring 124 is in its proximal position, illustrated in full line in FIG. 8, the cage 102 is radially collapsed and needle 130 fully retracted within the distal end of the shaft 106. The ring 124 can then be distally advanced, as shown in broken line in FIG. 8, and then rotated to lock in the advanced position. Such advancement deploys the cage 102, as shown in FIGS. 8B, 8C, and 8E, by advancing the inner member 116 relative to the outer member 118. Distally advancing the ring 124 also compresses a needle drive spring within the handle (not illustrated) simultaneously with deploying the cage 102. The needle drive spring is mechanically coupled to the needle 130, and relapse of the spring by depressing a release button 132 allows the needle to rapidly advance and cross the arterial and various walls. A needle retraction pull 134 is provide to allow the needle to be retracted when the catheter is to be withdrawn.

Figure 9:
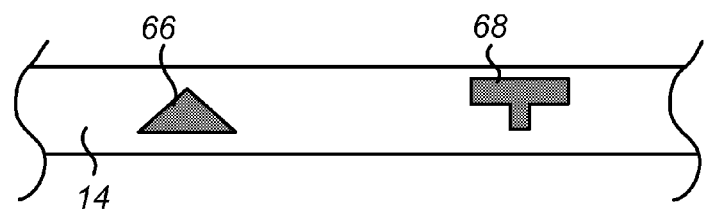
FIG. 9 illustrates exemplary rotational alignment markers which may be utilized on the shaft of the penetration catheter of the present invention.

Referring to FIG. 9, the penetration catheter 10 will typically include one or more rotational alignment markers, such as markers 66 and 68. The markers are placed on an exterior surface of the shaft near the distal end, as shown for example in FIGS. 3A-3C, and have a configuration which allows the physician to rotationally position the distal end 18 of the catheter shaft 14 so that the penetration tool 40 is properly aligned relative to the adjacent vessel into which the penetration tool 22 is to be advanced. The rotational alignment markers 66 and 68 will have geometries which appear different when observed under two-dimensional fluoroscopic imaging so that the rotational position of the penetration tool port 30 can be discerned.

Figure 9A:
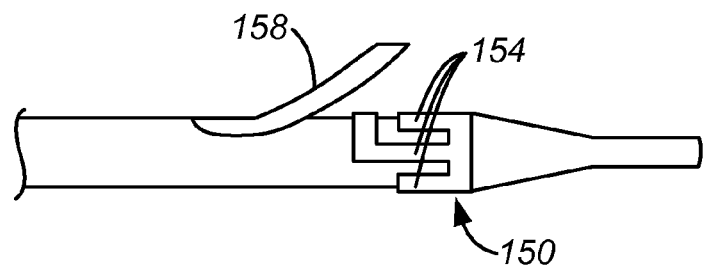
FIGS. 9A and 9B illustrate a second exemplary rotational alignment markers which may be utilized on the shaft of the penetration catheter of the present invention.
Figure 9B:
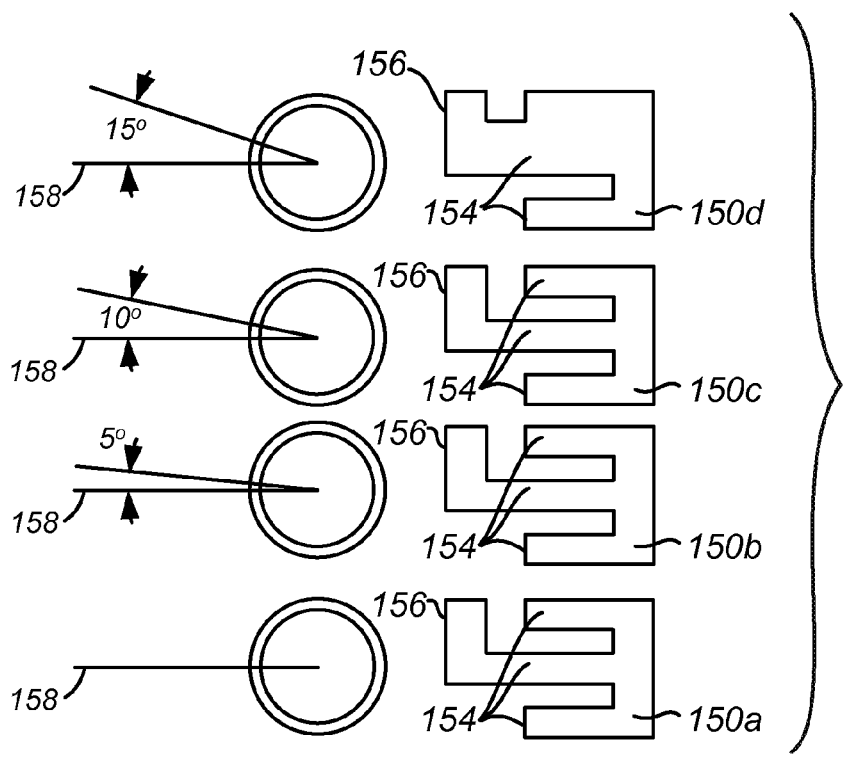

A presently preferred rotational alignment marker 150 is illustrated in FIGS. 9A and 9B. The rotational marker 150 typically comprises a radiopaque band secured around a catheter shaft 152 near its distal end. The radiopaque band 152 includes three axially aligned stripes 154. Each stripe has a substantially equal circumferential width, but the apparent width viewed fluoroscopically from above the shaft will vary depending on the angle at which the shaft is rotated about its axis. The middle stripe further includes a flag 156 which points toward a needle deployment direction 158. The rotational alignment marker 150 is particularly useful to rotationally align the catheter to deliver a needle in either a laterally right or laterally left direction. As seen in FIG. 9B, when the marker appears as shown in 150*a* under fluoroscopy, the needle is positioned to be directed in the lateral plane in the directions of the flag. As the catheter is progressively rotated out of alignment, as shown in 150*b*-150*d*, the symmetry of the stripes 154 is lost. Also, by rotating the catheter 180°, the needle will be directed to the opposite side and the direction of the flag 156 will also be reversed.

Figure 10A:
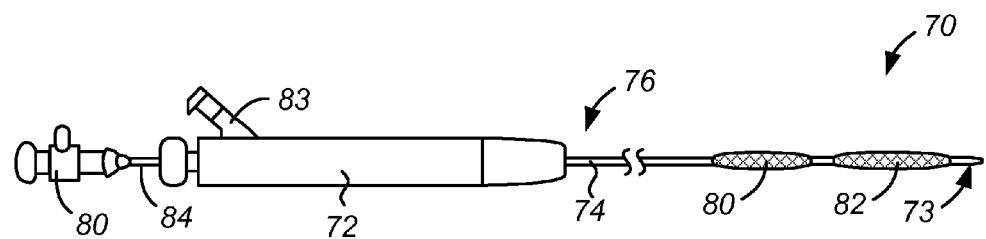
FIGS. 10A and 10B illustrate an exemplary guidewire capture and stabilization catheter which may be used in the systems and methods of the present invention.
Figure 10B:
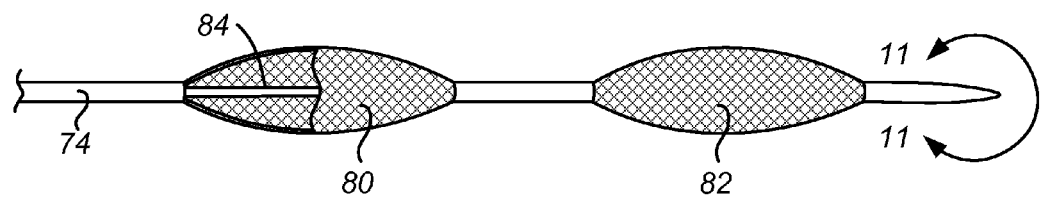
Figure 11:
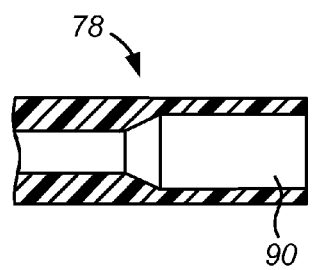
FIG. 11 is a detailed cross-sectional view of the distal end of the guidewire capture and stabilization catheter of FIGS. 10A and 10B illustrating a distal tip adapted to couple with a distal tip of the penetration catheter.

Referring now to FIGS. 10A, 10B, and 11, an exemplary guidewire capture and stabilization catheter 70 will be described. The guidewire capture and stabilization catheter 70 comprises a handle 72 (which may be a simple Y-shaped hub) connected to a proximal end 76 of a catheter shaft 74 having a distal end 78 which carries a proximal expandable cage 80 and a distal expandable cage 82. The cages are expandable from a radially collapsed configuration (as illustrated in FIG. 10A) to a radially expanded configuration (as shown in FIG. 10B). The cages will typically be formed from a shape memory material, such as nickel-titanium alloy, and will be woven or braided so that apertures or interstices between the woven or braided elements can receive the penetration tool 22 and guidewire advanced from the penetration catheter 10, as illustrated in detail below. In specific embodiments, the expandable cages 80 and 82 may be expanded in their unstressed conditions and be simultaneously collapsed by advancing an inner shaft 84 distally within the shaft 74. The inner shaft 84 is connected at or near the distal end of distal most cage 82 and a distal end of the shaft 74 is attached to a proximal end of the proximal most cage 80. In this way, distally advancing the inner shaft 84 relative to shaft 74 axially lengthens the cages causing them to radially collapse. In other embodiments, of course, the cages 80 and 82 could collapsed in their shelf or unstressed conditions and could be expanded by axially shortening using the same inner shaft 84. In still other embodiments, the cages 80 and 82 could be expanded in their shelf or unstrained configurations and could be collapsed using a separate outer sheath (not shown) which is retracted in order to allow the cages to radially expand. The same sheath could then also be used to secure a guidewire captured by the cages as the catheter is withdrawn.

The inner shaft 84 will typically have a hemostasis valve 86 at its proximal end to permit the shaft to be introduced over a guidewire. The handle 72 will include a flush port 88 to permit the introduction of fluids during the procedure.

The distal end 78 of the shaft will include a coupling receptacle 90 which is sized and adapted to engage and couple to the distal tip of the shaft 14 of the penetration catheter, as described in more detail below.

Figure 12C:
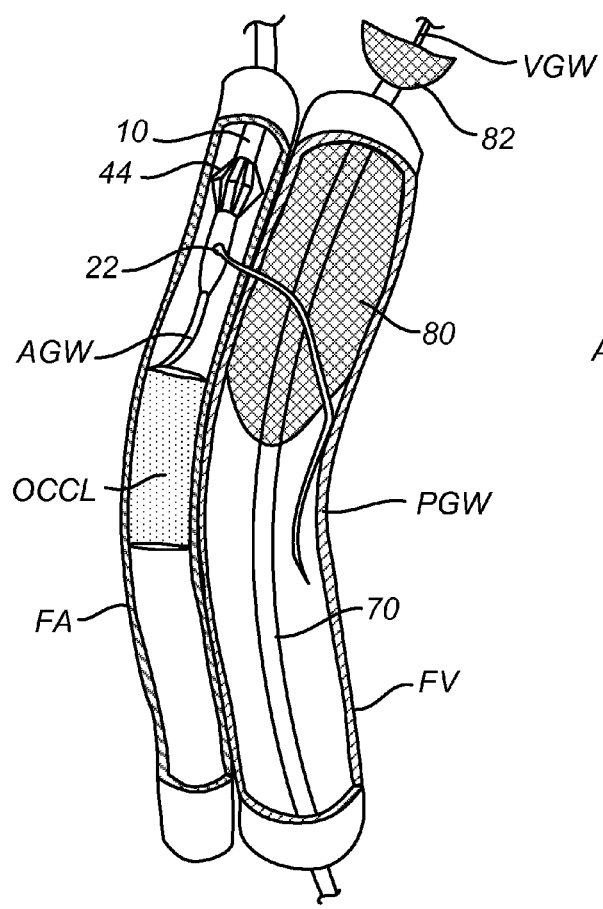

Referring now to FIGS. 12A-12J, use of the tools described above for performing methods in accordance with the principles of the present invention will be described. As shown in FIG. 12A, an arterial access guidewire AGW is introduced contralaterally from an access penetration AP, as shown in FIG. 1. The guidewire is advanced over the iliac artery bifurcation and down into the right femoral artery FA until it reaches the occlusion OCCL.

A venous guidewire VGW is introduced upwardly in the femoral vein FV, typically from a location in the popliteal vein PV (FIG. 1) or a tibeal vein beneath the popliteal vein. The venous catheter will typically be introduced under fluoroscopic guidance. The arterial guidewire AGW will typically be introduced first, although the relative timing of introduction of the two guidewires is not critical.

As shown in FIG. 12B, a penetration catheter 10 is introduced over the arterial guidewire AGW and oriented using rotational alignment marker 66 so that the penetration tool port 30 is aligned toward the femoral vein.

A guidewire capture and stabilization catheter 70 is introduced upwardly in the femoral vein over the venous guidewire VGW so that the proximal expandable cage 80 is aligned at a position above the occlusion OCCL in the adjacent femoral artery FA. Usually, the guidewire capture and stabilization catheter 70 will be introduced before the penetration catheter 10 so that the expanded proximal cage 80 can act as a fluoroscopic marker in aligning the penetration tool port 30 under fluoroscopic imaging and can support the relatively flaccid vein to facilitate entry of the penetration tool.

As illustrated in FIG. 12B and hereinafter, the penetration catheter 10 is illustrated as the embodiment of FIGS. 6A and 6B, described above. The single expandable cage 44 is expanded and located so that the penetration tool port 30 is at a desired distance above the occlusion OCCL. It will be appreciated that each of the other penetration tool embodiments (FIGS. 2-5) or others could have also been utilized in this method.

Figure 12D:
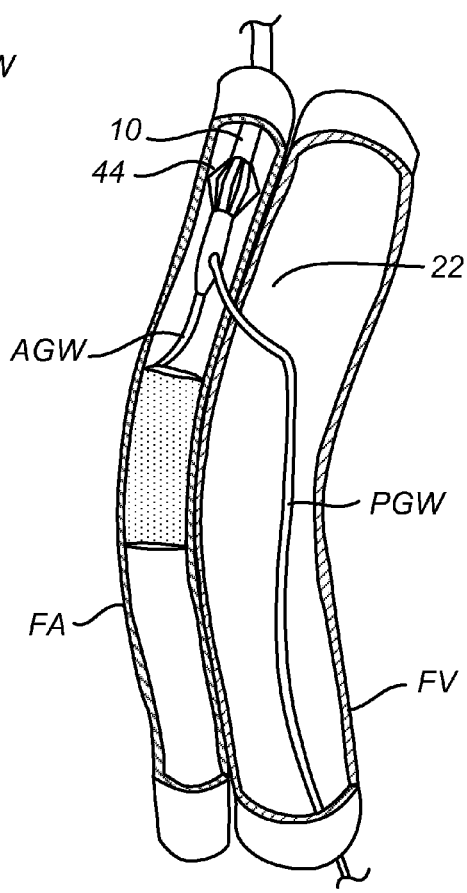
Figure 12E:
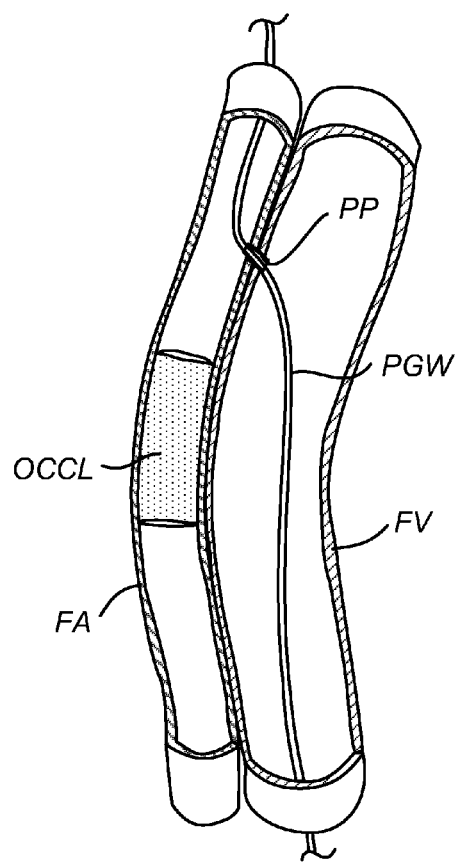

As shown in FIG. 12C, after the penetration catheter 10 and guidewire capture and stabilization catheter 70 are properly positioned and deployed, the penetration tool 22, typically a hollow needle having a sharpened distal tip but optionally any tubular or cannula member having a tissue-penetrating tip, such as an RF tip, at its distal end, is advanced from the lumen of the femoral artery into the deployed proximal cage 80 within the lumen of the femoral vein FV. Once penetration of the penetrating tool 22 into the cage 80 is confirmed under fluoroscopic imaging, the penetrating guidewire PGW is advanced from the tool 22 and downwardly out of the cage 80 into the lumen of the femoral vein. The penetration tool 22 is then retracted into the penetration catheter 10, and the proximal cage 80 is collapsed to capture the penetration guidewire PGW. After capturing the penetration guidewire, the guidewire capture and stabilization catheter 70 is withdrawn downwardly and removed from the lumen of the femoral vein FV so that the penetration guidewire PGW is drawn outwardly through the left percutaneous penetration, typically from the popliteal vein PV (FIG. 1), as shown in FIG. 12D.

After the penetration guidewire PGW has been properly placed, the penetration catheter 10 is removed, leaving the penetration guidewire extending from the contralateral introduction point AP (FIG. 1) to the venous penetration VP in the popliteal vein PV (FIG. 1). At this point, the proximal penetration PP (FIG. 12E) is typically dilated using a conventional balloon catheter. The catheter could be introduced through either penetration, and this step is not illustrated.

Figure 12F:
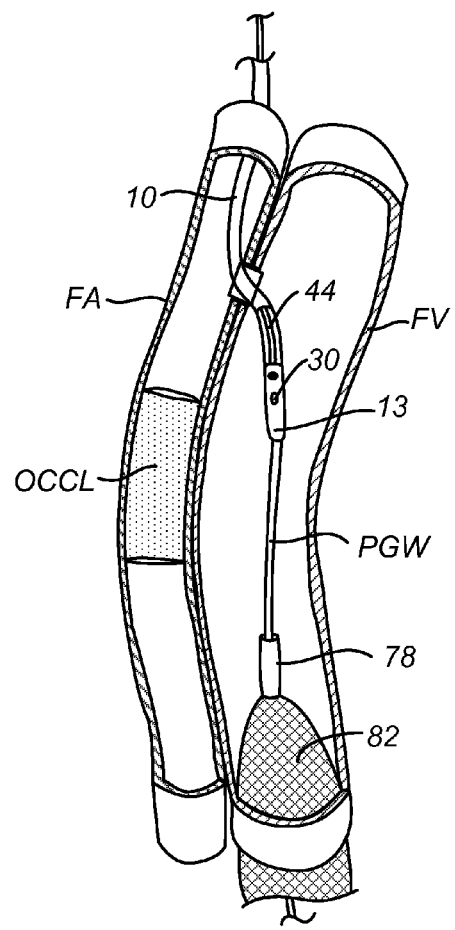

After the proximal penetration PP between the femoral artery FA and the femoral vein FV has been formed and dilated, penetration catheter 10 is reintroduced over the penetration guidewire PGW from the contralateral location, and the guidewire capture and stabilization catheter 70 is reintroduced over the penetration guidewire PGW from the penetration VP in the popliteal or tibeal vein. The order of introduction is not critical and the two catheters will both be advanced into the lumen of the femoral vein, as shown in FIG. 12F. Typically, however, the capture and stabilization catheter 70 and the cages 80 and 82 deployed to stabilize and centrally align the penetration catheter 10 as it is introduced.

The distal end 18 of the penetration catheter 10 is advanced so that it is received in the coupling receptacle 90 (FIG. 11) at the distal end 78 of the guidewire capture and stabilization catheter 70, as shown in FIG. 12G. Before completing such coupling, the distal end 18 of the penetration catheter is rotationally aligned, using marker 66, so that the penetration tool port 30 faces the lumen of the femoral artery FA. Once the penetration port 30 is properly aligned, the penetration catheter 10 and the guidewire capture and stabilization catheter 70 are coupled, and the distal cage 82 of the catheter 70 is expanded to stabilize and center the distal end 18 of the penetration catheter 10. The penetration tool 22 is then advanced into the lumen of the femoral artery 10 to form a distal penetration DPP, and an exchange guidewire EGW is advanced through the lumen of the tool 22 into the lumen of the femoral artery below the occlusion.

It is of note that the stabilization element, cage 44, of the penetration tool does not have to be used during this portion of the procedure. In fact, a completely separate catheter could be used without having this stabilization feature included in the catheter. For convenience and reduction of cost, however, it is desirable to re-use the same penetration catheter 10 which is used in forming the initial penetration PP on the proximal side of the occlusion OCCL.

Once the exchange guidewire EGW is in place, each of the penetration catheter 10, the guidewire capture and stabilization catheter 70, and the penetration guidewire PGW may be removed from the patient, leaving only the exchange EGW in place, as shown in FIG. 12H, extending from the contralateral penetration into the femoral artery FA to a location well below the occlusion OCCL where it re-enters the arterial lumen. The exchange guidewire is typically an 0.014 in. wire and is exchanged for an 0.035 stent placement guidewire SGW. Once the stent placement guidewire SGW is in place, the distal penetration DPP will typically be dilated using a conventional balloon angioplasty catheter which is introduced contralaterally over the stent placement guidewire. This dilation step is not illustrated.

Figure 12I:
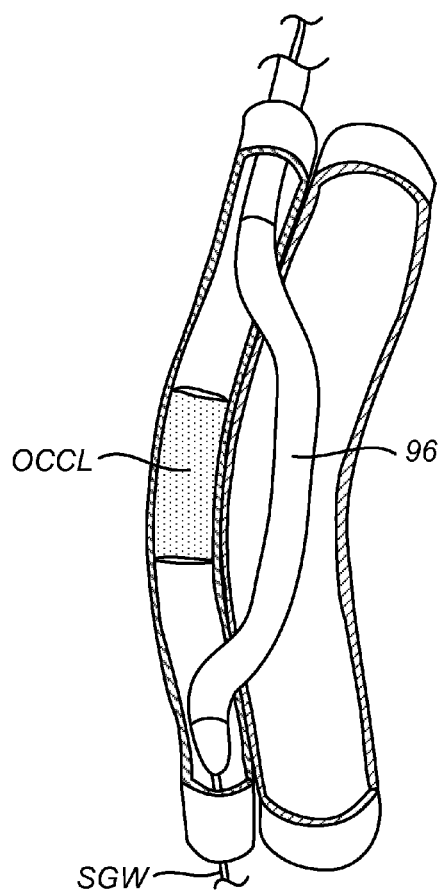
Figure 12J:
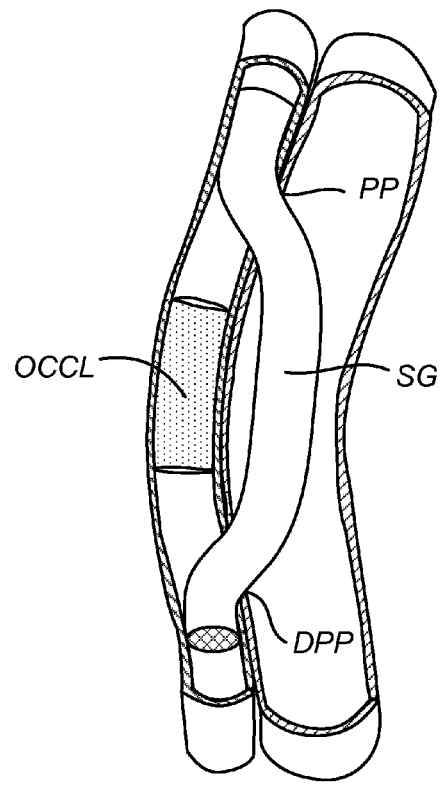

After dilation of the distal penetration DPP, a stent placement catheter 96 is introduced over the stent placement guidewire SGW from the contralateral penetration in the right femoral artery RFA (FIG. 1). The stent placement catheter 96 will carry a stent graft (or a plurality of stent grafts which can be formed in situ into an assembly of a desired length) capable of extending from the proximal penetration PP to the distal penetration DPP on either side of the occlusion OCCL, as shown in FIGS. 12I and 12J. Suitable stent graft(s) SG will typically be self-expanding, comprising a self-expanding inner stent or scaffold covered by an outer graft structure. Suitable stent-grafts and delivery catheters are commercially available. An exemplary stent graft that may be introduced using the tools and methods of the present invention is described in commonly owned U.S. patent application Ser. No. 13/422,594 (published as US2012/0239137), the full disclosure of which is incorporated herein by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for bypassing an occlusion in a peripheral artery, said method comprising:
   forming a proximal penetration from the peripheral artery to an adjacent peripheral vein at a location above the occlusion;
   advancing a penetration guidewire down the peripheral artery, through the proximal penetration, and into the peripheral vein;
   pulling the penetration guidewire through an external penetration below the occlusion;
   advancing a penetration catheter downward over the penetration guidewire from the peripheral artery into the peripheral vein;
   penetrating a penetration tool carried by the penetration catheter from the peripheral vein into the peripheral artery at a location below the occlusion to form a distal penetration; and
   placing a stent graft placement guidewire from the peripheral artery, through the proximal penetration, down the peripheral vein, and through the distal penetration back into the peripheral artery;
   deploying a stent graft from a catheter disposed over the stent graft placement guidewire.

2. A method as in claim 1, wherein forming the proximal penetration comprises:
   advancing a penetration catheter down the peripheral artery to a location above the occlusion; and
   penetrating a penetration tool carried by the penetration catheter from the peripheral artery into the peripheral vein.

3. A method as in claim 2, wherein the same penetration catheter is used for forming both the proximal and distal penetrations.

4. A method as in claim 2, wherein advancing the penetration guidewire comprises advancing the penetration guidewire through the penetration tool after said penetration tool has been penetrated from the peripheral artery into the peripheral vein.

5. A method as in claim 2, further comprising stabilizing the penetration catheter as the penetration tool is advanced from the peripheral artery into the peripheral vein.

6. A method as in claim 5, wherein stabilizing comprises radially expanding a stabilizing element on the penetration catheter to engage a wall of the peripheral artery.

7. A method as in claim 6, wherein the stabilizing element comprises a balloon, braid, or a malecot.

8. A method as in claim 1, wherein pulling the penetration guidewire comprises:
   advancing a venous catheter through the external penetration and up the peripheral vein to position a guidewire capture tool above the occlusion;

capturing the penetration guidewire with the guidewire capture tool; and withdrawing the venous catheter from the peripheral vein to pull the penetration guidewire through the external penetration.

9. A method as in claim 8, wherein the capture tool comprises an expandable braid and wherein capturing comprises collapsing the expandable braid over the penetration guidewire.

10. A method as in claim 8, further comprising stabilizing the penetration catheter as the penetration tool is advanced from the peripheral vein into the peripheral artery.

11. A method as in claim 10, wherein stabilizing comprises advancing the venous catheter through the external penetration and up the peripheral vein to connect to the penetration catheter as the penetration tool is advanced.

12. A method as in claim 11, wherein the venous catheter and penetration catheter are connected by coupling elements at a distal end of each catheter.

13. A method as in claim 11, further comprising radially expanding a stabilizing element on the venous catheter to engage a wall of the peripheral vein.

14. A method as in claim 13, wherein the stabilizing element comprises a balloon, braid, or a malecot.

15. A method as in claim 1, wherein placing the stent graft placement guidewire comprises advancing the stent graft placement guidewire through the penetration tool after said penetration tool has been advanced from the peripheral vein into the peripheral artery.

16. A method as in claim 1, wherein deploying the stent graft over the stent graft placement guidewire comprises releasing the stent graft from constraint, wherein the stent graft self-expands.

17. A method as in claim 16, wherein the stent graft is constrained in a tubular sheath wherein the tubular sheath is retracted to deploy the stent graft.

18. A method as in claim 1, wherein two or more stent grafts are deployed in an overlapping fashion.

19. A method as in claim 1, wherein the peripheral artery is selected from the group consisting of a superficial femoral artery, a common femoral artery, an iliac artery, a popliteal artery, a posterior tibial artery, an anterior tibial artery, and a perineal artery.

* * * * *